(12) United States Patent
Jansen et al.

(10) Patent No.: US 11,065,324 B2
(45) Date of Patent: Jul. 20, 2021

(54) COMBINATION VACCINE FOR SWINE

(71) Applicant: Intervet Inc., Madison, NJ (US)

(72) Inventors: Theodorus Jansen, Venray (NL); Maarten Hendrik Witvliet, Oostrum (NL)

(73) Assignee: Intervet, Inc., Madison, NJ (US)

( * ) Notice: Subject to any disclaimer, the term of this patent is extended or adjusted under 35 U.S.C. 154(b) by 34 days.

(21) Appl. No.: 16/471,606

(22) PCT Filed: Dec. 22, 2017

(86) PCT No.: PCT/EP2017/084376
§ 371 (c)(1),
(2) Date: Jun. 20, 2019

(87) PCT Pub. No.: WO2018/115435
PCT Pub. Date: Jun. 28, 2018

(65) Prior Publication Data
US 2020/0085935 A1   Mar. 19, 2020

(30) Foreign Application Priority Data

Dec. 23, 2016 (EP) ..................................... 16206789
Feb. 24, 2017 (EP) ..................................... 17157828

(51) Int. Cl.
| | |
|---|---|
| A61K 39/12 | (2006.01) |
| A61K 9/107 | (2006.01) |
| A61K 39/02 | (2006.01) |
| A61K 47/06 | (2006.01) |
| A61K 47/22 | (2006.01) |
| A61K 9/19 | (2006.01) |
| C12N 7/00 | (2006.01) |
| A61K 39/00 | (2006.01) |

(52) U.S. Cl.
CPC ............ *A61K 39/12* (2013.01); *A61K 9/1075* (2013.01); *A61K 9/19* (2013.01); *A61K 39/0241* (2013.01); *A61K 39/105* (2013.01); *A61K 47/06* (2013.01); *A61K 47/22* (2013.01); *C12N 7/00* (2013.01); *A61K 2039/5254* (2013.01); *A61K 2039/552* (2013.01); *A61K 2039/55566* (2013.01); *A61K 2039/70* (2013.01); *C12N 2750/10034* (2013.01); *C12N 2770/10034* (2013.01)

(58) Field of Classification Search
None
See application file for complete search history.

(56) References Cited

U.S. PATENT DOCUMENTS

| 5,667,784 A * | 9/1997 | Cornelius | A61K 39/39 424/204.1 |
|---|---|---|---|
| 2009/0136543 A1 * | 5/2009 | Ballou | C12N 7/00 424/206.1 |
| 2013/0266601 A1 | 10/2013 | Galvin | |
| 2013/0266602 A1 | 10/2013 | Nitzel | |
| 2013/0266603 A1 * | 10/2013 | Nitzel | A61K 39/0208 424/186.1 |
| 2016/0303219 A1 * | 10/2016 | Drexler | A61K 39/105 |

FOREIGN PATENT DOCUMENTS

| JP | 2015512448 A | 4/2015 |
|---|---|---|
| JP | 2015512449 A | 4/2015 |
| JP | 6078504 B2 | 1/2017 |
| JP | 2017501985 A | 1/2017 |
| JP | 6271504 B2 | 1/2018 |
| WO | 2009127684 A1 | 10/2009 |
| WO | WO 2009/127684 * | 10/2009 |
| WO | 2010092476 A1 | 8/2010 |
| WO | 2010094663 A1 | 8/2010 |
| WO | 2013152086 A1 | 10/2013 |
| WO | 2015082465 A1 | 6/2015 |

OTHER PUBLICATIONS

European Search Report for 16206789.6, dated Feb. 28, 2017, 7 pages.
Extended European Search report for 17157828.9 dated Jun. 8, 2017, 8 pages.
Garcon, N. et al., Development and evaluation of AS03, an Adjuvant System containing x-tocopherol and squalene in an oil-in-water emulsion, Expert review of Vaccines, 2012, pp. 349-366, 11:3.
International search report for application—PCTEP20170, dated Mar. 20, 2018, 4 pages.
Chen, Austen Y. et al., Evaluation of immune response to recombinant potential protective antigens of Mycoplasma hyopneumoniae delivered as cocktail DNA and/or recombinant protein vaccines in mice, Vaccine, 2008, 4372-4378, 26.
Djordjevic, S.P., et al., Serum and mucosal antibody responses and protection in pigs vaccinated against Mycoplasma hyopneumoniae with vaccines containing a denatured membrane antigen pool and adjuvant, Aust. Vet. J., 1997, pp. 504-511, vol. 75.
Drexler et al, Efficacy of combined porcine reproductive and respiratory syndrome virus and Mycoplasma hyopenumoniae vaccination in piglets, Veterinary Record, 2010, pp. 70-74, vol. 166(3).
Grau-Roma, Llorenc et al., Recent advances in the epidemiology, diagnosis and control of diseases caused by porcine circovirus type 2, The Veterinary Journal, 2011, 23-32, 187.

* cited by examiner

*Primary Examiner* — Shanon A. Foley

(74) *Attorney, Agent, or Firm* — Michael D. Davis

(57) ABSTRACT

The present invention relates to a combination vaccine for swine, comprising non-replicating antigen from porcine circovirus type 2 (PCV2), and live porcine reproductive and respiratory syndrome virus (PRRSV); the combination vaccine is formulated as an oil-in-water emulsion, and is adjuvated with squalane and vitamin E-acetate. This combination vaccine was found to be immunologically effective against all pathogens: PCV2, and PRRSV.

14 Claims, No Drawings

COMBINATION VACCINE FOR SWINE

CROSS-REFERENCE TO RELATED APPLICATIONS

This application is a national stage entry under 35 U.S.C. § 371 of PCT/EP2017/084376, filed on Dec. 22, 2017, which claims priority to EP Application 16206789.6, filed on Dec. 23, 2016 and EP Application 17157828.9, filed on Feb. 24, 2017, the content of PCT/EP2017/084376 is hereby incorporated by reference in its entirety.

The present invention relates to the field of veterinary vaccinology, namely to combination vaccines for swine. In particular the invention relates to a combination vaccine comprising non-replicating antigen from porcine circovirus type 2, and live porcine reproductive and respiratory syndrome virus. Also the invention relates to a kit of parts embodying the combination vaccine, and to methods for and uses of the combination vaccine.

Intensive swine farming today, relies heavily on veterinary medical products to keep animals healthy, and allow an economic operation. Next to optimisation of the feed and of farm management systems, a variety of treatments are regularly used: pharmaceuticals such as hormones or antibiotics, and vaccination against bacterial- or viral pathogens. Some of the most prominent diseases affecting swine from a young age onwards are caused by bacteria such as: *Mycoplasma hyopneumoniae* and *Lawsonia intracellularis*; and by viruses such as porcine circovirus type 2, and porcine reproductive and respiratory syndrome virus.

*Mycoplasma hyopneumoniae* (Mhyo) is the primary agent causing (porcine) enzootic pneumonia, a chronic respiratory disease in swine, occurring worldwide. Especially young piglets are vulnerable to this highly contagious disease. The bacterium is relatively small, lacks a cell wall, and belongs to the genus Mollicutes. These bacteria live a parasitic lifestyle on- or in host cells.

Pulmonary disease from Mhyo is largely an immune-mediated pathology leading to consolidated pneumonia. The bacterium colonizes and damages the pulmonary ciliated epithelium, leading to loss of cilliary activity. Depending on housing conditions and environmental stress, the most problematic consequence of this disease is that it predisposes for different secondary infections of the porcine respiratory system by other bacterial- and viral pathogens. This gives rise to the so called: Porcine Respiratory Disease Complex (PRDC), displaying severe lung lesions. Next to discomfort to the animal, enzootic pneumonia and PRDC cause important economic losses to the swine industry due to reduced performance in growth rate and feed conversion ratio, as well as through costs for veterinary care and antibiotics use.

*Lawsonia intracellularis* (*Lawsonia*) causes proliferative enteropathy, also known as ileitis, which is a common enteric disease of post-weaning pigs worldwide. The characteristic lesion is a proliferation of immature enterocytes in the ileal intestinal crypts, which cells contain the causative bacteria. Clearance of the bacteria from the enterocytes leads to resolution of the associated proliferative lesions. Histologic lesions can be confirmed as *Lawsonia*-positive by visualization of 1.5-2.5 µm long, vibrioid shaped bacteria in the enterocytes, but also within intestinal macrophages. The bacteria can be detected via PCR in clinical or in subclinical cases. Clinical cases are usually present in the grower-finisher period.

*Lawsonia* bacteria were first described in 1995 (McOrist et al., Int. J. Syst. Bact., vol. 45, p. 820-825). They are obligate intracellular, and non-motile gram-negative bacilli, from the Desulfovibrionaceae family.

Porcine circovirus type 2 (PCV2) is linked to the post-weaning multisystemic wasting syndrome (PMWS) observed in young pigs. The clinical signs and pathology were published in 1996, and include progressive wasting, dyspnoea, tachypnoea, and occasionally icterus and jaundice. The new agent was called PCV2 as being different from the known PCV, that was a natural contaminant of PK-15 cells.

PCV2 is a very small non-enveloped virus of the Circovirus genus. It contains a circular single stranded DNA genome with two major genes. The ORF2 gene encodes the viral capsid protein of about 233 amino acids. Recombinantly expressed PCV2 ORF2 proteins form virus like particles which are highly effective as a subunit vaccine.

Porcine reproductive and respiratory syndrome virus (PRRSV) was first reported in 1987, and in the early 1990's had become pandemic. It is a small, enveloped RNA virus of the Arterivirus genus, which contains a single-stranded, positive-sense, RNA genome. The virus causes significant losses in the swine industry due to reproductive disorders and growth retardation. Like Mhyo, PRRSV plays a significant role in the multifactorial PRDC. Clinical symptoms are abortions and stillborn or mummified foetuses, and cyanosis of the ear and vulva. In neonatal pigs, the virus causes respiratory distress, with increased susceptibility to secondary respiratory infections such as Glasser's disease (caused by *Haemophilus parasuis*). However subclinical infections are also common. The virus is quite variable: next to the European variant (type 1) and the North American variant (type 2), there is now a third genotype: a highly pathogenic variant which emerged in China in 2000, and is now causing severe disease in swine in Asia.

Commercial vaccines against each of these pathogens exist:

Against Mhyo a variety of commercial vaccines exist and these are routinely used in the majority of commercial swine farming operations. Generally these vaccines comprise non-replicating immunogens such as subunit proteins and/or bacterins (i.e. killed bacteria, intact or not), which are typically administered by parenteral injection. Some examples are: RespiSure™ (Zoetis), Ingelvac™ M. hyo (Boehringer Ingelheim), and M+Pac™ (Merck Animal Health).

Vaccines against *Lawsonia* are commercially available, e.g. Enterisol™ Ileitis (Boehringer Ingelheim Vetmedica, USA) which is a live attenuated vaccine, and Porcilis™ Ileitis (Merck Animal Health, USA) which is an adjuvated bacterin.

A vaccine against an infection with PCV2, can be based on whole inactivated PCV2 virus, e.g. Circovac™ (Merial), or inactivated chimeric PCV1/PCV2 virus (Suvaxyn™ PCV, Zoetis). More common are subunit vaccines of recombinant expressed PCV2 ORF2 protein, for example from a baculovirus-insect cell based expression system. Examples are: Porcilis™ PCV (MSD Animal Health), and Ingelvac CircoFlex™ (Boehringer Ingelheim).

Vaccines against PRRSV based on inactivated virus have been described and are commercially available. However vaccines based on live attenuated virus are considered more effective. Examples are: Porcilis™ PRRS (MSD Animal Health), Ingelvac PRRS™ MLV (Boehringer Ingelheim), and Fostera™ PRRS (Zoetis).

To limit stress to the animals and cost and labour for the caretakers, some swine vaccines have been prepared as combination vaccine. Examples are: Fostera™ PCV MH (Zoetis) and Porcilis PCV Mhyo (MSD Animal Health), which combine antigens from PCV2 and Mhyo.

Patent application WO 2013/152086 (Zoetis) describes a trivalent combination vaccine for swine, combining antigens from PCV2 and Mhyo with live PRRSV, however the described vaccine is not commercially available. Consequently there is an interest in this field for effective combination vaccines for swine against relevant swine diseases.

An important component of vaccines comprising non-replicating antigens is an adjuvant. This provides an immune-stimulation for the non-replicating antigen, which would otherwise not be immunogenic. This will trigger different routes of the immune system, the basic mechanisms are not well understood. In veterinary vaccines, a great variety of compounds can be used as adjuvant, for example: mineral oil e.g. Bayol™ or Markol™ Montanide™ or paraffin oil; non-mineral oil such as squalene, squalane, or vegetable oils, e.g. ethyl-oleate; aluminium salts, e.g. aluminium-hydroxide, or aluminium-phosphate; peptides such as dimethylglycine, or tuftsin; bacterial cell-wall components, such as lipid A and muramyldipeptide; (synthetic) polymers, such as pluronics, dextranes, carbomeres, pyran, or saponin; cytokines; and stimulators of toll-like receptors such as immunostimulatory oligodeoxynucleotides containing non-methylated CpG groups; etc.

The main problem to overcome in making adjuvated combination vaccines, is to prevent an interaction between the various vaccine components that would negatively influence the immune response or the vaccine's safety or stability. Such interaction may for instance occur between the antigens themselves, e.g. because some are quite crude products, such as the bacterins of Mhyo and of *Lawsonia*. Also, the adjuvant may interfere with, or even damage a vaccine antigen. Such an adverse interaction is of special relevance when the combination comprises a live microorganism. This is also recognised by the registration authorities providing marketing authorisations, for example: the USDA enforces regulation 9CFR 113.35 for detection of virucidal activity in an inactivated vaccine comprising a live virus.

These potential problems in the development of complex combination vaccines are generally recognised; see for example a publication from the EMEA: "Note for guidance: requirements for combined veterinary products" (EMEA, 2000, CVMP/IWP/52/97—FINAL); and a publication from the U.S. Department of Health and Human Services, Food and Drug Administration, Center for Biologies Evaluation and Research, from April 1997: "Guidance for Industry, for the evaluation of combination vaccines for preventable diseases: Production, Testing and Clinical Studies". Both these publications warn for the effects of interferences on the efficacy and safety of a vaccine, when combining antigens and adjuvants.

It is thus difficult to develop a combination vaccine which induces an effective immune-response against a combination of non-replicating antigens and a replicating microorganism, especially for complex combinations relating to multiple species of pathogens. Further the combination vaccine should be safe upon use in animals, i.e. not produce significant side reactions such as fever, local swelling, loss of appetite, etc. Also more practical properties are relevant:
the combination vaccine should ideally be capable of economic production, be sufficiently stable during formulation and storage, and allow potency testing methods for each antigen, in the presence of the other antigens.

It is therefore an objective of the present invention to overcome one or more disadvantages in the prior art, and to accommodate to a need in the field by providing an effective and safe combination vaccine for swine against disease associated with infection by PCV2 and PRRSV.

Unfortunately a straightforward combination of non-replicating antigen of PCV2, and live PRRS virus in an existing adjuvant formulation was not successful. For example: an adjuvant formulation that is used for several other swine vaccines is Xsolve™ (previously called: Microsol-Diluvac Forte™ MSD Animal health). This contains a combination of the adjuvants light mineral oil and vitamin E-acetate, with the emulsifier Tween™ 80. It is used e.g. for: Porcilis PCV (comprising PCV2 ORF2 antigen), Porcilis Ileitis (comprising *Lawsonia* bacterin), and Circumvent PCV-M G2 (comprising PCV2 and Mhyo antigens)

However a combination-vaccine of non-replicating antigens from Mhyo, *Lawsonia*, and PCV2 with live PRRSV in Xsolve, was not consistently effective. This mainly because of a virucidal effect on the live PRRSV component. In addition, Xsolve, like other adjuvants containing mineral oil, induces relatively strong vaccination reactions. While these are well within acceptable limits, improvement is desirable.

Similarly, a combination of these 4 antigens in an adjuvant known as Amphigen™ (Zoetis) also showed a virucidal effect on the PRRSV. Amphigen comprises mineral oil as adjuvant and lecithin as emulsifier.

Also, the adjuvant Emunade (mineral oil+ aluminiumhydroxide) was virucidal for live PRRSV.

One of the adjuvant formulations described in WO 2013/152086 (086) allegedly is not significantly virucidal for live PRRSV: a 10% dilution of formulation called "SP oil". This adjuvant is commercially available as Metastim™. Unfortunately, the exact composition of the formulation that was tested is not disclosed, but the preferred composition ranges of SP oil are given in the paragraph spanning pages 24-25 of '086. Using this SP oil at 10% dilution in a vaccine thus means the vaccine tested comprised: 0.1-0.3% v/v Pluronic™ 0.3-0.6% v/v squalane, and 0.01-0.05% v/v Tween 80.

'086 also recommends a number of other 'suitable' adjuvants ('086, page 25, lines 7-15), among which are Amphigen and Xsolve. However in practice these turned out not to be suitable; something that is also apparent from FIG. 10 of '086.

Another known vaccine adjuvant is AS03™ (GSK), which contains 2.1% w/v squalene and 2.4% w/v vitamin E, with 1.0% w/v Tween 80 as emulsifier. However this adjuvant is described for human application, and for antigen from a single species of pathogen, mainly inactivated human influenza virus. In addition, the use of AS03 has been scientifically linked to an increased risk of anaphylaxis, and to the induction of auto-immune disorders.

Further, while the monovalent Porcilis™ Mhyo vaccine is formulated in an aqueous solubilisate of vitamin E-acetate, however, when combined with PCV2 antigen an entirely different adjuvant and formulation were found to be optimal: the bivalent combination vaccine Porcilis PCV Mhyo is adjuvated with Emunade™ a mixture of mineral oil and aluminium-hydroxide, and the antigens need to be combined in a special way, as described in WO 2016/091998.

The ProSystem™ series of vaccines (Merck Animal Health) are a series of swine vaccines, containing a variety of non-replicative antigens from various bacterial species. These vaccines are aqueous formulations, adjuvated with aluminiumhydroxide gel. They are licensed for the resuspension of freeze-dried vaccines for swine with live attenuated viruses such as transmissible gastroenteritis virus and Rotavirus.

Different again regarding formulation and adjuvant used, is the trivalent combination vaccine 3Flex™ (Boehringer Ingelheim). This is marketed as 3 separate bottles with non-replicating antigens from Mhyo, and PCV2 combined with live PRRSV. These are to be mixed on the spot to form an aqueous composition with an adjuvant called Impranflex™ that contains Carbopol.

Over this plethora of options, the inventors had no indications which type of formulation and which type of adjuvant(s) to use for the development of a combination vaccine that was safe and stable, and effective against disease associated with infection by PCV2 and PRRSV.

Surprisingly it was found that this objective can be met, and consequently one or more disadvantages of the prior art can be overcome, by providing a combination vaccine for swine, comprising non-replicating antigen from PCV2 and live PRRSV, whereby the vaccine is formulated as an oil-in-water emulsion and is adjuvated with squalane and vitamin E-acetate.

A combination vaccine of this type and composition was found to be non-virucidal for the live PRRSV, and was effective in protecting swine against infections with PCV2 and PRRSV. Also the vaccine was safe for the target animals, could be economically produced, was stable upon formulation and storage, and allowed potency testing for all antigens in the final vaccine.

It is not known exactly why this particular formulation and this particular selection of adjuvants, is so favourable for this combination of antigens. Although the inventors do not want to be bound by any theory or model that might explain these findings, they speculate that the specific combination of squalane and vitamin E-acetate, in an oil-in-water formulation, provides just the right level of immunestimulation from these antigens, to be effective against their related diseases. This without causing significant vaccination side reactions, and apparently protecting the live PRRSV from significant virucidal effect of the adjuvant and the other antigens.

This was not at all evident from the prior art, as there is no other combination vaccine comprising these antigens. Also, some adjuvants described for other swine combination vaccines turned out not to be useful for this particular combination.

Therefore in one aspect the invention relates to a combination vaccine comprising non-replicating antigen from porcine circovirus type 2 (PCV2) and live porcine reproductive and respiratory syndrome virus (PRRSV), characterised in that the vaccine is an oil-in-water emulsion comprising squalane and vitamin E-acetate.

A "combination vaccine" is a vaccine comprising antigens from more than a single species of micro-organism.

A "vaccine" is well known to be a composition that has a medical effect. A vaccine comprises an immunologically active component, and a pharmaceutically acceptable carrier. The 'immunologically active component', is one or more antigenic molecule(s), here: non-replicating antigen from PCV2 and live PRRSV. These are recognised by the immune system of a target swine, and induce a protective immunological response. The response may originate from the targets' innate- and/or from the acquired immune system, and may be of the cellular- and/or of the humoral type.

A vaccine generally is efficacious in reducing the severity of an infection, for example by reducing the number of the pathogens, or shortening the duration of the pathogen's replication in a host animal.

Also, or possibly as a results thereof, a vaccine generally is effective in reducing or ameliorating the (clinical) symptoms of disease that may be caused by such infection or replication, or by the animal's response to that infection or replication.

The combination vaccine according to the invention induces in target swine a protective immune response, the effect of which is the prevention or the reduction of the severity of an infection by PCV2 and PRRSV. Also the combination vaccine prevents or reduces one or more signs of disease that are associated with such infection or replication. This translates to a positive effect on economic parameters such as: feed-conversion, average daily weight gain, carcass quality, and size and quality of litters. Observed effects of the combination vaccine according to the invention are:

for PCV2: reduction of virus load in blood and lymphatic tissues; in fattening pigs: reduction of mortality and loss of bodyweight;

and for PRRSV: For fattening pigs: reduction of respiratory disease with necrotising interstitial pneumonia, leading to improved growth and feed-conversion. For breeding pigs: reduction of trans-placental virus transfer, and improvement of reproductive failure such as: premature farrowing, and stillbirths or mummified piglets, and weakness and post-weaning respiratory disease in surviving piglets.

For infections with PCV2 and PRRSV, the induction of immuneprotection and thus the potency of the combination vaccine according to the invention, can be detected serologically as an increase in serum level of the pathogen specific antibodies, readily detectable using ELISA based techniques.

A combination vaccine according to the invention may colloquially also be referred to as a vaccine 'against' PCV2 and —PRRSV; or as an PCV2- and PRRSV vaccine.

Details and preferences of a combination vaccine according to the invention will be described herein below.

A "pharmaceutically acceptable carrier" for the invention is an aqueous liquid of a high grade of purity and preferably sterile, for example: water, a physiological salt solution, or a phosphate buffered saline solution. The carrier can comprise further additives, such as stabilisers or preservatives.

The term "comprising" (as well as variations such as "comprise", "comprises", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Thus any such text section, paragraph, claim, etc., can therefore also relate to one or more embodiment(s) wherein the term "comprising" (or its variants) is replaced by terms such as "consist of", "consisting of", or "consist essentially of".

"antigen" refers to molecules that can induce an immunological response under suitable conditions. Antigen can be prepared synthetically or be derived from a biological source, for example they can be a micro-organism or a part thereof.

"non-replicating" antigen relates to molecules such as proteins, carbohydrates, lipids or nucleic acids, or are complex combinations thereof, more or less pure. When prepared from a micro-organism, non-replicating antigen can refer to an intact but killed (i.e. non-replicative) micro-organism, or can be a part thereof such as an extract, fraction, homogenate, or sonicate. Also a non-replicating antigen can be a nucleic acid based, or recombinant product, such as an expression vector or an expressed protein, or the product of an in vitro expression system. All these are well-known in the art.

For the invention, the PRRSV is replicative.

"live PRRSV" refers to live PRRSV that are suitable for use as a vaccine component, i.e. having a reduced level of pathogenicity, also known as being attenuated, or modified live.

"attenuated" for the invention is defined as causing a lower level of lesions, and/or having a reduced rate of infection, or of replication. All, as compared to an unmodified or 'wildtype' PRRSV.

Attenuation of PRRSV can be obtained in vitro, for instance by passaging through experimental animals or in cell-culture and selection, or via recombinant DNA technology, all well known in the art.

While it is biologically incorrect to refer to a virus as being "live", that is the common way to refer to a virus that is not inactivated. Consequently, for the invention the term "live" as relating to PRRSV, refers to a PRRS virus that is capable of replication under appropriate conditions, e.g. in suitable host cells or animals.

"Porcine circovirus type 2" and "porcine reproductive and respiratory syndrome virus" all are well-known in the art as viruses, belonging to their respective genera and families. These induce diseases as described in well-known textbooks such as: "The Merck veterinary manual" (10th ed., 2010, C. M. Kahn edt., ISBN: 091191093X), or: "Diseases of Swine", 10th ed., Zimmerman edt., Wiley-Blackwell, Ames, Iowa, USA, ISBN: 081382267X.

Each of these pathogens displays the characterising features of its taxonomic group-members such as the morphologic, genomic, and biochemical characteristics, as well as the biological characteristics such as physiologic, immunologic, or pathologic behaviour.

As is known in the field, the classification of a micro-organism as a particular species is based on a combination of such features. The invention therefore also includes PCV2 or PRRSV that are sub-classified therefrom in any way, for instance as a subspecies, strain, isolate, genotype, variant, subtype or subgroup and the like.

It will be apparent to a skilled person that while a particular PCV2 or PRRSV for the invention may currently be assigned to a specific species, that is a taxonomic classification that could change in time as new insights can lead to reclassification into a new or different taxonomic group. However, as this does not change the micro-organism itself, or its antigenic repertoire, but only its scientific name or classification, such re-classified micro-organisms remain within the scope of the invention.

PCV2 and PRRSV for use in the invention can be obtained from a variety of sources, e.g. as field isolate from a porcine in the wild or on a farm, or from various laboratories, (depository) institutions, or (veterinary) universities.

An "oil-in-water emulsion" is a well-known composition, comprising an outer aqueous phase, which contains an internal dispersed oily phase. By the selection of the appropriate kind and concentration of emulsifier(s), such an emulsion can be formed. Procedures and equipment for the preparation of an oil-in-water emulsion for use as a vaccine are well-known in the art, and are for instance described in handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

For the invention, the outer aqueous phase comprises the non-replicating antigen from PCV2, and the live PRRSV in a pharmaceutically acceptable carrier; and the oily phase comprises squalane and vitamin E-acetate as adjuvants.

The combination vaccine according to the invention was found to be very effective, safe and stable, when prepared as an oil-in-water emulsion.

Embodiments and preferences for the manufacture of an oil-in-water emulsion for the combination vaccine according to the invention will be described herein below.

"squalane" refers to the chemical compound with CAS number 111-01-3. Some alternate names are: hydrogenated shark liver oil, hexamethyltetracosane, or perhydrosqualene. This is not to be confused with squalene (CAS nr. 111-02-4) which is a poly-unsaturated C30 oil and is metaboliseable as a compound of the cholesterol pathway. However, squalane is the fully hydrogenated form of squalene and is therefore not prone to oxidation. Thus, while squalane is a non-mineral oil, and is transported from the injection site, it is non-metaboliseable.

Originally the precursor to squalane was obtained from shark livers, but over environmental concerns this has shifted to other natural sources, such as olive oil, or to chemical synthesis. Therefore included in the definition of squalane are natural, synthetic or semi-synthetic forms, or mixtures thereof. Squalane is commercially available in a variety of purities, for example: from vegetable source, from Worlee (Squalane, vegetable), or Croda (Pripure Squalane); or synthetic, e.g. from Kuraray (Squalane-PE). For the invention, a high purity of the squalane is preferred: preferably over 75% purity, more preferably over 80, 90, or even over 95% purity, in that order of preference.

"vitamin E-acetate" refers to the chemical compound with CAS number 58-95-7. Some alternate names are: tocopheryl acetate, or alpha-tocopherol-acetate. Vitamin E-acetate is an acetate-ester of vitamin E (tocopherol), and can be derived from vegetable materials such as seeds, nuts, fruits or leaves, or from fatty meats, but may also be produced synthetically. Thus, included in the definition of vitamin E-acetate are natural, synthetic or semi-synthetic forms, or mixtures thereof. Vitamin E-acetate is commercially available, in different degrees of purity.

For the invention, the non-replicative antigen of PCV2 is preferably: ORF2 protein.

Each of the antigens in the combination vaccine according to the invention can be of a single type, or can be of multiple types, e.g. from one or from more than one strains of the respective pathogen.

The squalane in the combination vaccine according to the invention is present in an amount of between about 1 and about 9% w/v of the vaccine. More preferably, squalane is present in an amount of between 2-7% w/v, or even 2-5% w/v of the vaccine, in that order of preference.

Most preferred: squalane is present in an amount of about 3.4% w/v of the vaccine.

Therefore, in an embodiment of the combination vaccine according to the invention, the vaccine comprises squalane in an amount of between about 1 and about 9% w/v.

For the invention "about" indicates that a number can vary between ±25% around its indicated value. Preferably "about" means±20% around its value, more preferably "about" means±15, 12, 10, 8, 6, 5, 4, 3, 2% around its value, or even "about" means±1% around its value, in that order of preference.

The vitamin E-acetate in the combination vaccine according to the invention is present in an amount of between about 1 and about 10% w/v of the vaccine. More preferably, vitamin E-acetate is present in an amount of between 2-8% w/v, or even 3-5% w/v of the vaccine, in that order of preference.

Most preferred: vitamin E-acetate is present in an amount of about 4% w/v of the vaccine.

Therefore, in an embodiment of the combination vaccine according to the invention, the vaccine comprises vitamin E-acetate in an amount of between about 1 and about 10% w/v.

The inventors found that the use of squalane and vitamin E-acetate in these amounts in the combination vaccine according to the invention was advantageous in adjuvating an immune response against each of the pathogens: PCV2 and PRRSV, and providing stability. Surprisingly however, this did not cause any significant vaccination side reactions when administered to target swine, nor cause any significant virucidal effect on the live PRRSV.

The vitamin E-acetate for use in the combination vaccine according to the invention is preferably DL-alpha-tocopherol-acetate, which is the racemate of the chemical with CAS number: 7695-91-2.

In an embodiment of the combination vaccine according to the invention, the antigens are:

For the non-replicative antigen of PCV2: the ORF2 protein is obtained from a recombinant expression system, or is delivered and expressed via a replicon particle; a replicon particle is a defective alphavirus particle, as developed by AlphaVax. The parental PCV2 of the ORF2 sequence that is expressed, can be of any of the PCV2 seroytypes a, b, c, or d, or can be from a chimera from one or more of these serotypes.

For PRRSV: the live attenuated virus is from one or more genotypes, for example type 1, type 2 and/or type 3. More preferred: the live PRRSV is an attenuated version from strain DV or strain Nebraska.

In an embodiment of the vaccine according to the invention, the pharmaceutically acceptable carrier is water. Preferably the water is of a high degree of purity, such as double distilled-, micro-filtrated-, or reversed-osmosis water. More preferred: the water is water-for-injection, and is sterile and essentially free from pyrogens.

A convenient feature of vaccines based on oil-in-water emulsions, is that the antigens are usually in the water phase. This means that the oily phase can be prepared and emulsified in water separately, employing methods and techniques that would not as such be compatible with maintaining the quality or the viability of the vaccine antigens. For example using high-energy emulsification at high temperatures. This generates an oily emulsion for the invention, which is an oil-in-water emulsion of squalane, vitamin E-acetate and polysorbate 80 in water.

To prepare the combination vaccine according to the invention, the aqueous phase with the antigens, and the oily emulsion with the adjuvants are combined by gentle mixing at room temperature.

The combination of the two compositions causes a dilution of each of them. Consequently each needs to be prepared as an intermediary composition in which the concentration of the various components is higher than it will be in the final vaccine, by a factor equal to the dilution that will be applied. Typically aqueous phase and oily emulsion can be mixed in a volume ratio anywhere between 10:90 and 90:10.

The combination vaccine according to the invention preferably comprises an aqueous phase and an oily emulsion-both as described-, in a volume ratio between about 20:80 and about 80:20.

Therefore in an embodiment, the combination vaccine according to the invention is prepared from the admixture of an aqueous phase and an oily emulsion, in a volume ratio between about 20:80 and about 80:20.

Preferably the volume ratio is between about 30:70 and about 70:30; between about 40:60 and about 60:40; or even the volume ratio is about 50:50, in that order of preference.

Evidently, when the combination ratio of aqueous phase and oily emulsion is 50:50, then each of the two compositions should comprise its various components in an amount or in a concentration that is two times higher than desired in the final vaccine formulation that is prepared from the combination of the two intermediary compositions.

In a preferred embodiment, the oily emulsion for the invention is prepared using an emulsifier with an HLB value (hydrophilic-lipophilic balance) of between about 8 and about 20; a preferred emulsifier is polysorbate 80.

Polysorbate 80 refers to a chemical with CAS nr. 9005-65-6, also named: polyoxyethylene sorbitan monooleate. It has HLB value 14, and is widely commercially available, e.g. as Tween 80.

Preferably polysorbate 80 is present in the combination vaccine according to the invention in an amount of between about 0.1 and about 5% w/v of the vaccine. More preferably, polysorbate 80 is present in an amount of between 0.3-3% w/v, 0.5-2.5%, or even 1-2% w/v of the vaccine, in that order of preference.

Most preferred: polysorbate 80 is present in an amount of about 1.6% w/v of the vaccine.

Therefore, in an embodiment, the combination vaccine according to the invention comprises polysorbate 80 in an amount of between about 0.1 and about 5% w/v.

An oily emulsion for the invention, can be prepared at any scale and using any suitable homogenisation equipment, such as from: Silverson, Ultra Turrax™, or a Dispax reactor (IKA). The skilled person can perform and optimise such an emulsification process to control the size of the particles of the dispersed phase (here: the oily adjuvants). Together with the choice of type- and concentration of the emulsifier(s), this controls the pharmaceutical properties of the emulsion, and also its stability. The main parameters of the emulsification process itself are: the energy input (power and rpm), the temperature, the duration, and the number of repeat cycles. Details of embodiments of the emulsification process are presented below.

The size of the particles of the dispersed phase is preferably quite small. When the diameter of the particles of the dispersed phase is below about 1 micrometre, such emulsions are commonly called "submicron emulsions".

In an embodiment of the oil-in-water emulsion of the combination vaccine according to the invention, the emulsion is a submicron emulsion.

Equipment to measure particle sizes of 1 micrometre or less is generally available, for example by laser diffraction measurement. Typically particle size is expressed in nanometres (nm), and as an average particle size, also known as median diameter, expressed as the D50 of a cumulative particle size distribution.

For the invention, particle size is expressed in nm of D50, as determined using a Mastersizer™ (Malvern Instruments). Particle size measurements can be made in the (concentrated) oily emulsion or in the combination vaccine; the particle refractive index of the oily phase for the invention is 1.48. The Malvern Mastersizer size analysis report presents D50 as D(0.50). All this is well-known to a skilled person.

There are many ways available to produce such submicron emulsions, typically by the use of a high-energy emulsification process, for example using: high-pressure homogenisers, rotor-stator devices, blenders, ultrasonic waves, microporous membranes, or microchannelling devices.

Preferred process for high-energy emulsification for the invention, is the use of a high-pressure homogeniser, preferably a Microfluidiser™ (Microfluidics). Typically 3 passages at a pressure of between 500-1500 bar (i.e. 7000-22000 psi) will be sufficient.

Emulsions prepared in this way typically have dispersed phase particles with a D50 of 500 nm or less, and have a narrow size distribution; for the invention, the dispersed phase are the droplets of the oily adjuvants.

Typically emulsions with such very finely sized particles of the dispersed phase, are prepared in several steps. In this way, an initial relatively coarse oily emulsion is prepared by low-energy mixing, which is followed by one or more subsequent high-energy treatments to achieve further reduction of particle size.

Next, the 'microfluidised' oily emulsion, comprising the adjuvants and emulsifier in water is then combined with the aqueous phase comprising the antigens, to prepare the combination vaccine according to the invention.

Therefore, in an embodiment of the submicron oil-in-water emulsion of the combination vaccine according to the invention, the oil-droplets have a D50 of 500 nm or less; preferably D50 is 250 nm or less. More preferred: D50 is 150 nm or less.

For reasons of product consistency and -quality, not only the median particle diameter, but also the spread in particle size, also known as the size distribution, can advantageously be monitored and controlled. The size distribution of the oil-droplets in the submicron oil-in-water emulsion of the combination vaccine according to the invention is preferably relatively narrow. An indicator of particle size distribution is the D90 of a cumulative particle size distribution.

Therefore, in an embodiment of the submicron oil-in-water emulsion of the combination vaccine according to the invention, the oil-droplets have a D90 below 900 nm, more preferred D90 is below 500 nm, 400 nm, or even below 300 nm, in that order of preference. Most preferred: D90 is about 250 nm.

One of the advantages of the emulsion having such small particle size, and -distribution, is that this can then be sterilised by filtration, without significant loss of material. This because typical sterilisation filters have a pore size of about 0.2 micrometres. Such filter sterilisation overcomes the need for other methods of sterilisation that may be damaging to the quality of the components of the oily emulsion, such as by: heating, chemicals, or irradiation.

Depending on the circumstances of the intended use of the combination vaccine according to the invention, e.g. field conditions, or specifics of target species, it may be preferred to optimise the vaccine. This is well within the capabilities of a skilled person, and generally involves the fine-tuning of the efficacy, safety, or stability of the vaccine.

A combination vaccine according to the invention comprises the non-replicative antigen from PCV2, and live PRRSV, in amounts that are capable of inducing in the swine target a protective immune response against their associated diseases, as described above.

A skilled person in the field of the invention will be more than capable of determining the effectiveness of a combination vaccine according to the invention, e.g. by monitoring the immunological response following vaccination or after a challenge infection, e.g. by monitoring the targets' signs of disease, clinical scores, or by re-isolation of the pathogen, and comparing these results to a vaccination-challenge response seen in mock-vaccinated animals.

As an indication, the amounts of the antigens to be used in the combination vaccine according to the invention can be based on those used in the respective monovalent- or combination vaccines with these antigens. For example, the combination vaccine according to the invention can comprise per millilitre: of PCV2: 1-50 µg ORF2; and of PRRSV: $10^3$-$10^6$ TCID50. Methods to quantify these antigens are well-known in the art, and can also rely on ELISA based quantification against specific standards.

The combination vaccine according to the invention can advantageously be combined with one or more further antigens, replicative or non-replicative, whole or disrupted. However the combination is preferably made with care to safeguard the stability and efficacy of the overall combination vaccine, and the viability of the replicative vaccine components. Such choices are within the routine capabilities of the skilled person.

Therefore, in an embodiment the combination vaccine according to the invention comprises at least one additional antigen.

The additional antigen is either an attenuated form of a micro-organism which is pathogenic to swine, or is a non-replicative antigen derived from a micro-organism pathogenic to swine. The micro-organism may be any virus, bacterium, parasite, fungus, *rickettsia*, protozoa and/or parasite that is pathogenic to swine.

Examples of such micro-organisms pathogenic to swine are: pseudorabies virus, porcine parvo virus, classical swine fever virus, swine influenza virus, foot-and-mouth disease virus, porcine epidemic diarrhoea virus, transmissible gastro enteritis virus, porcine respiratory coronavirus, vesicular stomatitis virus, *Mycoplasma hyopneumoniae, Lawsonia intracellularis, Actinobacillus pleuropneumoniae, Brachyspira, E. coli, Haemophilus, Streptococcus, Salmonella, Clostridia, Pasteurella, Erysipelothrix, Leptospira, Bordetella, Toxoplasma, Isospora*, and *Trichinella*.

Preferred additional antigens are one or more from: *Mycoplasma hyopneumoniae, Lawsonia intracellularis, Actinobacillus pleuropneumoniae, Haemophilus parasuis, Brachyspira hyodysenteriae*, and swine influenza virus.

Therefore in a preferred embodiment the combination vaccine according to the invention also comprises non-replicating antigen from *Mycoplasma hyopneumoniae* (Mhyo).

In an alternate preferred embodiment the combination vaccine according to the invention also comprises non-replicating antigen from *Lawsonia intracellularis* (*Lawsonia*).

The non-replicating antigens from Mhyo and *Lawsonia* are preferably a bacterin.

For the invention, a "bacterin" is a composition comprising inactivated (killed) bacteria, whereby the inactivated bacteria may be whole intact cells, or may have become damaged to some extent by the inactivation, or a mixture thereof, e.g. as in a whole inactivated culture.

The Mhyo or *Lawsonia* bacterin is preferably a killed whole cell-culture. The Mhyo bacterin is preferably from strain 11 or strain J. NB: Mhyo was formerly called *M. suipneumoniae*.

The amounts of the antigens to be used in the combination vaccine according to the invention can be: of Mhyo: 2-20% w/v of an inactivated concentrated Mhyo culture; and/or of *Lawsonia*: inactivated whole cells at between $1 \times 10^7$ and $1 \times 10^{10}$ cells.

Observed effects of the combination vaccine according to the invention are:

for Mhyo: prevention or reduction of lung lesions caused by Mhyo, such as consolidated pneumonia, and chronic respiratory disease;

for *Lawsonia*: reduction of colonisation and faecal shedding by *Lawsonia*, and reduction of signs of ileitis with intestinal hyperplasia, porcine haemorrhagic enteropathy, or porcine intestinal adenomatosis;

For *Lawsonia*, the potency of the combination vaccine according to the invention, can be detected serologically as an increase in serum level of *Lawsonia* specific antibodies, readily detectable using ELISA based techniques.

For Mhyo, the most reliable measure of vaccine potency is the reduction of lung lesion scores after Mhyo challenge infection. Such lesions are typically scored during necropsy by macroscopic assessment of lung consolidation, based on the Goodwin scale (Goodwin et al., 1969, J. Hyg. Camb., vol. 67, p. 465-476); this scale runs from zero up to a maximum of 55 points/animal for totally affected lungs.

A combination vaccine according to the invention can advantageously be combined with a pharmaceutical compound such as an antibiotic, a hormone, and/or an anti-inflammatory drug.

A combination vaccine according to the invention can comprise further excipients, to optimise the efficacy or the stability of the vaccine, such as stabilisers or preservatives. Examples of stabilisers are: milk-powder, gelatine, serum albumin, sorbitol, trehalose, amino acids, spermidine, dextrane or polyvinyl pyrrolidone. Examples of preservatives are: thimerosal, merthiolate, phenolic compounds, or gentamicin.

When the antigens used in the combination vaccine according to the invention are specially selected, the combination vaccine can be used as a so-called marker vaccine. This means that the immunity caused by the vaccine against one of the pathogens, can be differentiated by some method of detection from the immune-response that would occur upon an infection of a target with the wild type pathogen. This is also known as DIVA: "differentiation of infected from vaccinated animals". The vaccine thus has a positive or negative 'marker' as compared to a wild type infection.

Therefore, in an embodiment, the combination vaccine according to the invention is a marker vaccine.

In an embodiment, the combination vaccine is for swine.

The term "swine" refers to animals of the family Suidae, and preferably to animals of the genus Sus, which are also referred to as porcines. Examples are: a wild or a domestic pig, hog, wild boar, babirusa, or warthog. This also includes swine indicated by an arbitrary name, for example referring to their sex or age such as: sow, queen, boar, barrow, hog, gilt, weaner, or piglet.

Further the term swine refers to porcine animals of any type such as of breeding- or fattening type, and to parental lines of any of these types.

Further or additional embodiments of the combination vaccine according to the invention are conceivable, and are perfectly achievable for a skilled person. Also these further embodiments may be applied in one or more combination(s) to the embodiments already described.

Therefore in an embodiment of a combination vaccine according to the invention, one, more, or all of the conditions apply, selected from the group consisting of:

the combination vaccine comprises squalane in an amount of between about 1 and about 9% w/v; preferably squalane is comprised in an amount of between 2-5% w/v;

the combination vaccine comprises vitamin E-acetate in an amount of between about 1 and about 10% w/v; preferably vitamin E-acetate is comprised in an amount of between 3-5% w/v;

the vitamin E-acetate is preferably DL-alpha-tocopherol-acetate;

the combination vaccine is prepared from the admixture of an aqueous phase and an oily emulsion, in a volume ratio between about 20:80 and about 80:20;

the combination vaccine comprises polysorbate 80 in an amount of between about 0.1 and about 5% w/v; preferably polysorbate 80 is comprised in an amount of between 1-2% w/v;

the oil-in-water emulsion is a submicron emulsion; more preferably the oil-droplets have a D50 of 500 nm or less.

the combination vaccine comprises at least one additional antigen; preferably one or more antigen from: *Actinobacillus pleuropneumoniae, Haemophilus parasuis, Brachyspira hyodysenteriae*, and swine influenza virus;

the combination vaccine is also comprising non-replicating antigen from *Mycoplasma hyopneumoniae;* the combination vaccine is also comprising non-replicating antigen from *Lawsonia intracellularis;* the combination vaccine is a marker vaccine; and the combination vaccine is for swine.

In an embodiment of the combination vaccine according to the invention, the vaccine comprises squalane in an amount of between about 1 and about 9% w/v; the vaccine comprises vitamin E-acetate in an amount of between about 1 and about 10% w/v; the vitamin E-acetate is DL-alpha-tocopherol-acetate; the vaccine is prepared from the admixture of an aqueous phase and an oily emulsion, in a volume ratio between about 20:80 and about 80:20; the vaccine comprises polysorbate 80 in an amount of between about 0.1 and about 5% w/v; the oil-in-water emulsion is a submicron emulsion; and the vaccine is for swine.

The combination vaccine according to the invention can be composed in different ways, as described herein.

One advantageous way to prepare the combination vaccine according to the invention, is by reconstitution of a freeze-dried preparation of live PRRSV. For example an incomplete version of the combination vaccine according to the invention, not yet containing PRRSV, can be used as diluent for a freeze-dried preparation of a live attenuated PRRSV, conveniently: an existing freeze-dried live PRRSV vaccine such as e.g. Porcilis PRRSV, or Prime Pac™ PRRS+.

Consequently, the combination vaccine according to the invention can be produced from a kit of parts, comprising at least two containers: one container comprising all components of the combination vaccine according to the invention except for the live PRRSV virus; and one container comprising a live attenuated PRRSV in freeze-dried form. The elements of the kit of parts then together embody the combination vaccine according to the invention.

Therefore in a further aspect, the invention relates to a kit of parts comprising at least two containers: one container comprising non-replicating antigen from PCV2 in an oil-in-water emulsion comprising squalane and vitamin E-acetate; and one container comprising live PRRSV in freeze-dried form.

Upon the reconstitution of the live PRRSV the complete combination vaccine according to the invention is formed. This is also referred to as mixing the vaccine 'on-the-spot', or 'field-side' mixing.

Although the combination vaccine is not virucidal to the PRRSV, it is preferred to do the reconstitution shortly before the administration of the vaccine, to assure the best quality of the vaccine.

Preferably the reconstitution is performed within 8 hours of administration, more preferably within 6, 5, 4, 3, or even within 2 hours before administration, in this order of preference.

The kit of parts according to the invention, and its elements, can comprise any of the embodiments (preferred or not) as described herein for the combination vaccine according to the invention, or any combination of two or more of those embodiments of the combination vaccine according to the invention.

A further advantageous utility of the kit of parts according to the invention, is one wherein both the non-replicating antigen from *Lawsonia* and the live PRRSV are taken-up into the combination vaccine according to the invention by reconstitution of a freeze-dried preparation.

Therefore in an embodiment, the kit of parts according to the invention comprises at least three containers: one container comprising non-replicating antigen from PCV2, in an oil-in-water emulsion comprising squalane and vitamin E-acetate; one container comprising live PRRSV in freeze-dried form; and one container comprising non-replicating antigen from *Lawsonia* in freeze-dried form.

In a preferred embodiment of the kit of parts according to the invention comprising at least three containers, the container comprising the non-replicating antigen from PCV2 in an oil-in-water emulsion comprising squalane and vitamin E-acetate, also comprises non-replicating antigen from Mhyo.

The freeze-dried form can be a freeze-dried cake in a container, e.g. a bottle, but can also be a lyosphere as applied in the Sphereon™ technology.

Because of the nature of a freeze-dried body, its reconstitution does not significantly (i.e. less than about 5%; more preferred: less than about 1%) change the volume of the diluent used. Consequently, the preparations of the combination vaccine according to the invention with all components except for the live PRRSV, or with all components except for the live PRRSV and the non-replicating antigen from *Lawsonia*, that are to be provided in the kit of parts according to the invention, can be provided essentially with its other components in the final amounts or at their final concentrations.

The combination vaccine according to the invention can be prepared from the respective antigens and excipients, by methods that are well known in the art, and are within the routine capabilities of a person skilled in the art. For example: PCV2 ORF2 can be expressed by a recombinant baculovirus in an insect cell culture, and harvested; alternatively the PCV2 ORF2 protein can be delivered and expressed using a replicon particle (supra). PRRSV can be cultured on appropriate host cells, e.g. primary pig macrophages, or a cell-line such as Marc-145 or MA104.

These antigens are quantified, and taken up into an aqueous phase in the required amounts. This can be either with or without the non-replicating antigens from Mhyo, *Lawsonia* and/or the live PRRSV; this in case the combination vaccine according to the invention is to be commercialised as a kit of parts according to the invention.

Separately, the oily emulsion with adjuvants and emulsifier in water, is prepared by an emulsification process. Next, this is mixed with the aqueous phase with the antigens, in a desired volume ratio.

The various stages of the manufacturing process are monitored by adequate tests, for instance by microbiological and immunological tests for the quality and quantity of the bacteria and viruses, or any further antigens; by tests for absence of extraneous agents; tests for chemical and biological stability; and ultimately by in vitro or in vivo experiments to determine vaccine efficacy and -safety. All these are well known to a skilled person, and are prescribed in Governmental regulations such as the Pharmacopoeia, and in handbooks such as: Remington and Pastoret (both supra).

Therefore in a further aspect the invention relates to a method for the preparation of a combination vaccine according to the invention, comprising the steps of:
preparing an aqueous phase comprising non-replicating antigen from PCV2, and live PRRSV, and
admixing said aqueous phase with an oily emulsion comprising squalane and vitamin E-acetate.

As described, the method for the preparation of a combination vaccine according to the invention can advantageously be adapted to incorporate antigen from Mhyo, or from *Lawsonia* and/or from live PRRSV in a later stage, for example by reconstitution of separate freeze-dried preparations of these antigens.

Therefore in a further aspect the invention relates to a method for the preparation of a combination vaccine according to the invention, comprising the steps of:
preparing live PRRSV in a freeze-dried form,
preparing an aqueous phase comprising non-replicating antigen from PCV2,
admixing said aqueous phase with an oily emulsion comprising squalane and vitamin E-acetate, and
reconstituting said freeze-dried live PRRSV with said admixture of aqueous phase and oily emulsion.

The aqueous phase comprising non-replicating antigen from PCV2 optionally comprising non-replicating antigen from Mhyo.

Similarly,

In a further aspect the invention relates to a method for the preparation of a combination vaccine according to the invention, comprising the steps of:
preparing live PRRSV in a freeze-dried form,
preparing non-replicating *Lawsonia* antigen in a freeze-dried form,
preparing an aqueous phase comprising non-replicating antigen from PCV2,
admixing said aqueous phase with an oily emulsion comprising squalane and vitamin E-acetate, and reconstituting said freeze-dried live PRRSV and said non-replicating *Lawsonia* antigen with said admixture of aqueous phase and oily emulsion.

The aqueous phase comprising non-replicating antigen from PCV2 optionally comprising non-replicating antigen from Mhyo.

Or in a similar embodiment: the invention relates to a method for the preparation of a combination vaccine according to the invention, comprising the steps of:

preparing an admixture of an aqueous phase comprising non-replicating antigen from PCV2, and of an oily emulsion comprising squalane and vitamin E-acetate, and reconstituting live PRRSV in a freeze-dried form with said admixture.

The aqueous phase comprising non-replicating antigen from PCV2 optionally comprising non-replicating antigen from Mhyo.

At different points in these methods, additional steps may be added, for example for additional treatments such as for purification or storage. Also the method for the preparation can involve the admixing with an additional antigen, or pharmaceutically acceptable excipients such as stabilisers or preservatives.

These variations, and optionally many more, can be incorporated as a further step at an appropriate point in the method for preparation according to the invention.

Therefore the methods for the preparation according to the invention can comprise any of the embodiments (preferred or not) as described herein for the combination vaccine according to the invention, or any combination of two or more of those embodiments of the combination vaccine according to the invention.

As described, the combination vaccine according to the invention, which can be prepared by a method according to the invention, can advantageously be used for the administration to swine, to protect against infection by and/or disease associated with an infection by PCV2 and PRRSV.

Therefore in a further aspect the invention relates to an oil-in-water emulsion comprising squalane and vitamin E-acetate, non-replicative antigen from PCV2 and live PRRSV, for use in vaccination of swine against PCV2 and PRRSV.

Alternatively:

In a further aspect the invention relates to the use of non-replicative antigen from PCV2 and of live PRRSV, for the manufacture of a combination vaccine for swine, characterised in that the vaccine is an oil-in-water emulsion comprising squalane and vitamin E-acetate.

The combination vaccine according to the invention can be applied for the vaccination of swine against PCV2 and PRRSV.

Therefore in a further aspect the invention relates to a method for the vaccination of swine against PCV2 and PRRSV, by administration to said swine of an oil-in-water emulsion comprising squalane and vitamin E-acetate, non-replicative antigen from PCV2 and live PRRSV.

Or in a similar embodiment: the invention relates to a method for the vaccination of swine against PCV2 and PRRSV, by administration to said swine of a combination vaccine according to the invention.

An oil-in-water emulsion such as the combination vaccine according to the invention, is preferably administered by some way of parenteral administration, e.g. through all routes of injection into or through the skin: e.g. intramuscular, intravenous, intraperitoneal, intradermal, submucosal, or subcutaneous. This can be achieved in different ways, for example using a classic syringe and hypodermic needle.

Alternatively the parenteral administration may be done by some method of needle-free injection, delivering the vaccine by an intradermal, or transdermal applicator such as the IDAL™.

In an embodiment of the method of vaccination according to the invention, the administration is applied by intramuscular route.

The volume of an animal dose of the combination vaccine according to the invention is not critical provided an effective immunoprotection is obtained. This may be different for the different routes of administration such as: intramuscular, subcutaneous, or intradermal. Preferably the volume of one animal dose is between about 0.1 and 10 ml per animal; more preferably between 0.2 and 5 ml, 0.5 and 3, or even between 0.5 and 2 ml per animal dose, in that order of preference.

Therefore in an embodiment of the method for administration according to the invention, the combination vaccine according to the invention is administered in a dose of between about 0.1 and 10 ml per animal.

The administration regime for a method of vaccination according to the invention, to a target swine can be in single or in multiple doses, or in a manner compatible with practical aspects of swine husbandry.

When required, a swine target may be given second or further administrations of the combination according to the invention, later in life, so-called booster vaccinations. However the combination vaccine according to the invention is optimised in such a way that a single vaccination dose will generally suffice to provide an immune protection during the relevant period of life of the swine, for example during the fattening stage of the swine up to 6 months of age.

Thus in a preferred embodiment, the combination vaccine according to the invention is administered only once per swine target, i.e. it is a single-dose vaccine.

Preferably, the regime for the method of vaccination is integrated into existing vaccination schedules of other vaccines that the target swine may require, in order to further reduce stress to the animals and to reduce labour costs. These other vaccines can be administered in a simultaneous, concurrent, or sequential fashion, in a manner compatible with their registered use.

Therefore in an embodiment of the method of vaccination of swine according to the invention, the combination vaccine according to the invention is administered in a combination with another swine vaccine.

Target swine for a vaccination for the invention can be of any age in which they are susceptible to the vaccination, and/or are susceptible to the disease or the infection against which the vaccine protects.

Further the weight, sex, immunological status, etc. of the target swine for a vaccination according to the invention, are not critical although it is favourable to vaccinate healthy targets, and to vaccinate as early as possible to prevent (the consequences of) an early infection with Mhyo, *Lawsonia*, PCV2, or PRRSV.

Therefore, in an embodiment of the method of vaccination of swine according to the invention, the combination vaccine according to the invention is administered to young swine.

For the invention, "young swine" are swine to about 2 months of age.

Because of the high prevalence of Mhyo, *Lawsonia*, PCV2, and PRRSV, and because of the widespread use of vaccines against one or more of these pathogens, many swine sows will be seropositive for antibodies against one or more of Mhyo, *Lawsonia*, PCV2, and PRRSV. Consequently, young swine that consumed colostrum from such sows, will be MDA+(maternally derived antibody positive). This is no hindrance to the efficacy of the combination vaccine according to the invention, as it is effective also in MDA+ swine.

Therefore in an embodiment of the method for vaccination according to the invention, the combination vaccine according to the invention is administered to MDA+ swine.

PRRSV specifically induces respiratory disease in adult swine.

Therefore in an embodiment of the method of vaccination of swine according to the invention, the combination vaccine according to the invention is administered to adult swine.

For the invention, "adult swine" are swine from about 6 months of age.

The administration of a combination vaccine according to the invention can be applied either as a prophylactic- or as a therapeutic treatment, or both, as it interferes both with the establishment and with the progression of an infection by Mhyo, *Lawsonia*, PCV2, and PRRSV.

The use of the combination vaccine according to the invention will assist in the reduction of infection by one, or all of Mhyo, *Lawsonia*, PCV2, and PRRSV, in a swine herd, on a farm, or in swine in a geographical area.

Therefore, in a further aspect the invention relates to a method for the reduction of an infection with Mhyo, *Lawsonia*, PCV2, or PRRSV, or of associated signs of disease in swine, characterised in that the method comprises the administration to said swine of a combination vaccine according to the invention.

The invention will now be further described by the following, non-limiting, examples.

EXAMPLES

1. Preparation of the Combination Vaccine

The combination vaccine according to the invention was prepared as follows:

The oily emulsion in 2× concentration contains per 100 g:
Polysorbate 80 (Tween 80): 3.24 g;
Squalane: 6.75 g;
DL-alpha tocopherol acetate: 7.94 g;
water for injection: 82.07 g.

This oily emulsion was prepared according to the following subsequent process steps:
required amounts of Tween 80 and squalane were weighed off, and combined in a beaker
the Tween 80/squalane mixture was homogenised by low-energy mixing (magnetic stirrer), at room temperature,
the required amount of DL-alpha tocopherol acetate was weighed off, and added to the homogenised Tween 80/squalane mixture
the combined mixture was homogenised again, by low-energy mixing at room temperature,
the mixture was heated to 65-75° C.
the water for injection was heated to 65-75° C.
the heated oil-phase and the water were pre-mixed using high energy mixing by Ultra Turrax with N18 rod, for 5-15 minutes; the temperature decreased from 65 to 55° C.
the pre-mix was given 3 passages through a Microfluidiser at 800 bar; temperature was kept below 50° C. with a cooling spiral.
the microfluidised oily emulsion was sterilised by filtration through an 0.2 micrometre filter (Pall, Ultipor™ N66); the filter had been preheated to 55-75° C. via its double wall.

Of the final oily emulsion (in 2× concentrate), completeness and level of homogenisation were checked by light-microscopy. Further pH (7.34), and osmolality (221 mOsm/kg) were also checked. Particle size measurements revealed: D100=300 nm; D99=250 nm; D90=200 nm, and D50=130 nm.

The aqueous phase (in 2× concentration) was prepared by taking the required amount of each of the non-replicating antigens: Mhyo: 6% v/v of a 10× concentrated inactivated culture; *Lawsonia*: 2×10^9 inactivated cells; and PCV: 50 µg ORF2.

Next, both concentrated compositions (oily emulsion with adjuvants, and aqueous phase with antigens) were combined in 50:50 volume ratio, by low-energy mixing at room temperature.

This vaccine mixture was used to resuspend ampules of Porcilis PRRS, with the required volume to reach a full dose of PRRSV (10^5 TCID50) per 2 ml of the combination vaccine.

The final combination vaccine contained: 3.375% w/v squalane; 3.97% w/v vitamin E-acetate, and 1.62% w/v Tween 80, and had a density of 0.9913 g/ml. Products were stored at 2-8° C.

2. Test for Virucidal Effect

The oily emulsion of the invention was incubated with a sample of live PRRSV, to determine if any virucidal effect would occur.

In short: an ampule of Porcilis PRRSV was reconstituted in PBS to a final volume of 7 ml, to reach a titre of 6 Log 10 TCID50/ml. A 50 µl sample of this virus suspension was combined with 450 µl of a combination vaccine without live PRRSV, prepared as in Example 1, and comprising: squalane, vitamin E-acetate, and polysorbate 80, microfluidised in water, with non-replicating antigens of Mhyo, *Lawsonia* and PCV2. A control sample of PRRSV was mixed with 450 µl PBS. Both samples were incubated for 1 hour at room temperature. Next the incubated samples were titrated to determine the remaining titre of PRRSV.

Titration was done on 1 day old monolayers of MA104 cells. 10 rows of starting wells received 25 µl of incubated virus sample, this was diluted 1:10 through 7 subsequent wells. 2 columns of untreated cells served as negative controls. This was done in duplo. Next the plates were incubated for 3 days at 37° C. in 5% CO2 atmosphere. Finally PRRSV viral replication was detected by Immuno-fluorescence using an anti-PRRSV monoclonal antibody and a fluorescently labelled detection antibody. Titres were calculated using the Spearman-Kaerber algorithm.

| Sample | Titre[1] (Log10 TCID50/ml) |
|---|---|
| combination vaccine (0.9×) | 4.6 |
| control | 4.8 |

[1]Titre is the average of two determinations

With a spread in titration values found of ±0.2 Log 10 TCID50, the results demonstrated that samples of live PRRSV incubated in an 0.9× concentrated combination vaccine according to the invention, did not experience a significant reduction of titre.

3. Vaccination-Challenge Experiment 3.1. Introduction

A combination vaccine without live PRRSV, prepared as in Example 1, and comprising: squalane, vitamin E-acetate, and polysorbate 80, microfluidised in water, with non-replicating antigens of Mhyo, *Lawsonia* and PCV2, was tested in animals. Vaccination was given as a one shot dose, by intramuscular route, at 3 weeks of age. Mhyo efficacy was tested by challenge infection, at 4 weeks post vaccination. Several other adjuvants were compared.

3.2. Study Design

84 SPF piglets were used for this study. 6 groups of 12 animals were vaccinated once intra-muscularly at the age of three weeks (+/− three days). One group of 12 pigs was left unvaccinated and served as challenge-control group. Prior to vaccination and two days after vaccination rectal temperatures were measured. Furthermore, for the SVEA group, injection sites were palpated weekly for local reactions. Four weeks after vaccination all animals were infected with a virulent Mhyo strain. Three weeks post-challenge all animals were euthanized and investigated post-mortem for lung lesions. From all animals, blood samples were taken: prior to vaccination, before challenge and at post-mortem.

TABLE 1

Schedule of treatment of Example 3

| Group | Vaccine-adjuvant |
|---|---|
| 1 | Amphigen |
| 2 | SVEA |
| 3 | SVEA + Al(OH)3 |
| 4 | MF59 + DDA |
| 5 | SP oil (Metastim) |
| 6 | Vaxliant S5 |
| 7 | no vaccine |

3.3. Adjuvants Tested

A number of vaccine formulations were tested, which differed only in respect of the type of formulation and adjuvant used; antigen content was the same. The following adjuvants were tested:

Amphigen: oil-in-water of mineral oil with lecithin
SVEA: microfluidised oil-in-water emulsion with squalane, vitamin E-acetate and Tween 80
SVEA+Al(OH)3: SVEA with 0.2% w/v aluminiumhydroxide (same as in Porcilis PCV Mhyo)
MF59+ DDA: MF59 is an oil-in-water emulsion with squalene, polysorbate 80 and Span 85; DDA is a cationic lipid: dimethyldioctadecylammonium.
SP oil: pluronic, squalane and Tween, as described in WO 2013/152086.
Vaxliant™ S5: proprietary adjuvant of unknown composition 3.4. Methods and Materials Challenge:

Challenge material was Mhyo, virulent field strain, fresh 3 day culture in FRIIS medium with porcine serum. 10 ml culture containing 9 CCU, was administered intra-tracheally per animal, on two consecutive days. All animals were under regular veterinary supervision Vaccination:

Vaccination was at three weeks, while animals were still with their sow. Dose was 3 ml, given intramuscularly, at right side of the neck. Weaning was at 4 weeks of age. One week prior to challenge pigs were transferred to challenge facilities.

Serology:

Blood samples (from vena jugularis) were taken just before vaccination (T=0), just before challenge (T=4) and at post-mortem (T=7). Samples were kept at ambient temperature, till serum was derived. Presence of relevant antibodies in serum samples for PCV2 (via Elisa), or for *Lawsonia*, was determined according to standard procedures.

Palpation

Injection sites of the SVEA group were inspected for local reactions: just before vaccination, four hours after vaccination, daily for two days and weekly for five weeks after vaccination. Animals that still showed local reactions five weeks after vaccination were palpated individually weekly until local reactions disappeared.

Rectal Temperatures and Clinical Observations

Rectal temperatures were measured and clinical observations (0=Normal; 1=less active; 2=vomiting; 3=lies down) were done one day before, and just before vaccination, four hours and one and two days after vaccination.

Post Mortem Examination

At the end of this experiment, 3 weeks after challenge, all pigs were euthanized. Injection sites were investigated for local reactions in individual animals. Percentage lung lesion score was recorded for each pig individually according to Goodwin & Whittlestone score.

3.5. Results

TABLE 2

Results of Example 3

| Group | Vaccine adjuvant | Mhyo LLS[1] | PCV2 Ab titre[2] at x weeks p.v. | | | Lawsonia Ab titre at x weeks p.v. | | |
|---|---|---|---|---|---|---|---|---|
| | | | 0 | 4 | 7 | 0 | 4 | 7 |
| 1 | Amphigen | 1.5 | 8.2 | 8.1 | <6.7 | <4.2 | <5.7 | <6.8 |
| 2 | SVEA | 0.75 | 8.2 | 9.3 | 8.9 | <4.1 | 7.3 | 9.1 |
| 3 | SVEA + Al(OH)3 | 2 | 8.1 | 8.7 | <7.6 | <4.2 | 7.6 | 9.6 |
| 4 | MF59 + DDA | 0.5 | <7.9 | 7.7 | <6.4 | <4.2 | <4.7 | <4.6 |
| 5 | SP oil (Metastim) | 0 | 8.6 | 8.0 | <6.9 | <4.2 | 6.7 | 8.4 |
| 6 | Vaxliant S5 | 0 | 7.5 | <7.1 | <6.3 | <4.0 | <4.6 | <6.1 |
| 7 | no vaccine | 3.5 | 8.0 | <6.4 | <4.8 | <4.1 | <4.1 | <3.9 |

[1]Mhyo LLS = median lung lesion score

Results of Palpations and Temperature:

The group monitored by palpation of vaccination site and checked for temperature was the group receiving vaccine adjuvated with SVEA (group 2). These showed that no detectable local swelling, and no rise in temperature was observed throughout the monitoring period.

3.6. Conclusions

Table 2 demonstrates that broad efficacy for a combination vaccine is hard to achieve; several of the adjuvants tested, did induce for one or even two of the pathogens an immunity that could be assigned as protective; this either in terms of low Mhyo lung lesion score, or as sufficiently high specific antibody titre for PCV2 and *Lawsonia*. However only for the SVEA adjuvanted vaccine, was protection sufficient to good for all three pathogens. None of the other adjuvants came to that level of broad efficacy.

The data from Example 2, on the lack of virucidal effect of SVEA adjuvated combination vaccine for live PRRSV, predict that a combination vaccine with SVEA adjuvant will also be effective against PRRSV.

Together this demonstrates that a combination vaccine according to the invention is immunologically effective against each of the pathogens Mhyo, *Lawsonia*, PCV2, and PRRSV. Further it is safe for swine.

4. Four-Way Vaccination-Challenge Experiments

Further vaccination-challenge experiments were performed, whereby pigs were vaccinated with the four-way combination vaccine according to the invention, and in 4 separate experiments this vaccine was tested for efficacy of all the 4 components: Mhyo, *Lawsonia*, PCV and PRRSV.

Specifically, a 3-way combination vaccine was prepared as described in Examples 1 and 3, containing a submicron emulsion of squalane, vitamin E acetate, and Tween 8, mixed 1:1 with an aqueous phase comprising inactivated antigens of Mhyo and *Lawsonia*, and recombinant expression product of PCV2-ORF2. Subsequently, and shortly before vaccination of pigs, this 3-way vaccine was used to dissolve an ampule of freeze-dried commercial PRRS vaccine, using the required volume to reach a full dose of PRRSV of 10^5 TCID50, per 2 ml animal dose of the 4-way combination vaccine. Vaccination was given as a one-shot dose, by intramuscular route, to pigs at 3 weeks of age.

Subsequent analysis of the vaccine efficacy of each of the four vaccine antigens was done in separate experiments, by challenge infection of the vaccinates and controls, to allow focus on the specific symptoms of infection and disease for these different conditions.

However, no differences in outcome of vaccination-efficacy against any of these challenge infections was expected as compared to the results described in Example 3 above; it was highly unlikely that there would be any different effect of the use of a 3-way as compared to a 4-way vaccine in respect of the protection against the inactivated antigens. In other words, the presence of PRRSV virus in the 4-way combination vaccine could not be expected to affect the efficacy of that combination vaccine against any one of the Mhyo, *Lawsonia*, or PCV challenge infections. Further, no effect was expected on the viability and efficacy of the live PRRSV component, as the previous experiments had already indicated that there was no significant effect of the 3-way vaccine in SVEA adjuvant on the viability of PRRS virus. Consequently, as the PRRS virus was not killed or its infectivity damaged by mixing into the 3-way vaccine, there was no reason why it would not be able to induce effective protection.

These expectations were indeed confirmed by the results of the 4 challenge experiments described below: the 4-way combination vaccine according to the invention was found to induce effective immune protection against infection and signs of disease induced by a challenge infection with a pathogen from each of its 4 components. Also, there was no negative effect or interference from its combination.

4.1. *M. Hyopneumoniae* Efficacy

The 4-way combination vaccine was prepared as described above, using Porcilis PRRS freeze dried vaccine.

Experimental Outline

24 SPF piglets were used for this study. 1 group of 12 animals was vaccinated once intra-muscularly at the age of about three weeks. One group of 12 pigs was left unvaccinated and served as challenge-control group. Four weeks after vaccination all animals were challenge-infected with a virulent Mhyo strain. Three weeks post-challenge all animals were euthanized and investigated post-mortem for lung lesions. From all animals, blood samples were taken: prior to vaccination, before challenge and at post-mortem.

Details of the Experiment

Challenge material was from an Mhyo virulent field strain, as fresh 3 day culture in FRIIS medium with porcine serum. 10 ml culture containing 10 and 9 CCU, respectively, was administered intra-tracheally per animal, on two consecutive days. All animals were under regular veterinary supervision Vaccination was at three weeks of age, while animals were still with their sow. The dose was 2 ml, given intra-muscularly, at the right side of the neck. Weaning was at 4 weeks of age. One week prior to challenge pigs were transferred to challenge facilities.

Blood samples (from vena jugularis) were taken just before vaccination (T=0 weeks), just before challenge (T=4 weeks) and at post-mortem (T=7 weeks). Samples were kept at ambient temperature, till serum was derived. Presence of relevant antibodies in serum samples for PCV2, or for *Lawsonia*, was determined by ELISA according to standard procedures.

Data Analysis:

At the end of this experiment, 3 weeks after challenge, all pigs were euthanized. Percentage lung lesion score was recorded for each pig individually according to the Goodwin & Whittlestone score (supra).
Results

TABLE 3

Results of Mhyo and serology data of Example 4.1

| Group | Vaccination | Mhyo LLS [1] | PCV2 Ab titre at 7 weeks p.v. | | | Lawsonia Ab titre at 7 weeks p.v. | | |
|---|---|---|---|---|---|---|---|---|
| | | | 0 | 4 | 7 | 0 | 4 | 7 |
| 1 | 4-way in SVEA | 8.0 | <4.8 | 10.6 | 9.9 | <3.9 | <6.6 | 9.2 |
| 2 | no vaccine | 12.7 | 5.4 | <4.8 | <4.3 | <3.9 | <3.9 | <3.9 |

[1] Mhyo LLS = median of lung lesion scores

Conclusion

Vaccination of pigs with the 4 way combination vaccine according to the invention, was effective in protecting against infection and signs of disease induced by an Mhyo challenge infection. Also, there was a good development of protection against Lawsonia and PCV2, as measured by serology.

4.2. PCV2 Efficacy

The 4-way combination vaccine was prepared as described above, using Porcilis PRRS freeze dried vaccine.

Experimental Outline & Details of the Experiment

Piglets were allotted to treatment groups of 10 piglets each. The piglets were vaccinated intradermally or intramuscularly when they were approximately five weeks old:
one group was vaccinated intramuscularly with the 4-way combination vaccine in SVEA adjuvant: a single 2 ml dose of vaccine formulated with PCV2-Orf2 (2500 AU/ml), Mhyo (1.0 PCVU/ml), Lawsonia (5000 AU/ml), and PRRSV at $10^5 TCID_{50}$/dose. Time between dissolving the PRRS vaccine and vaccination was 1 hour.

group 2 was the positive control, and this was vaccinated using the commercial vaccines Porcilis PCV ID and Porcilis PRRS ID, both by intra-dermal route, but non-mixed and given at different sites on the back of the pigs.

piglets in the third group were not vaccinated (negative control group), but were challenged.

At three weeks post vaccination (8 weeks of age, 3 weeks post vaccination, sample date [SD]22 days) all animals were challenged using 5.0 $\log_{10} TCID_{50}$/mL of wild-type PCV2b challenge virus, strain 112/11, which was inoculated intranasally, at 3 ml per nostril.

Three weeks post challenge, all animals were necropsied and inguinal lymph node, mesenteric lymph node, tonsil and lung were sampled for the detection of PCV2, bt qPCR, and by immunhistochemistry.

All piglets were observed daily after vaccination for clinical signs. Temperatures were taken at SD-1, SD0, SD0+4 hours and SD1.

Serum samples were collected from all animals, these were tested for antibodies against PCV2, PRRSV and Lawsonia.

Serum, tissue, and fecal- and nasal swab samples were collected from all animals, and were examined for PCV nucleic acid by qPCR.

Data Analysis & Results:

Temperature readings showed no significant results.

Combined serological results are represented in Table 4 below.

PCV2 Serology:

All piglets from the two vaccinated groups reached 100% seroconversion for anti-PCV2 antibodies already at sample date 22 (3 weeks p.v.). Actual titres increased some more after that, and reached a plateau from SD35. Unvaccinated controls only seroconverted after challenge, but never reached more than 20% seroconversion.

PCV2 IHC and qPCR:

Immunohistological screening and scoring was performed for signs of PCV in lymphnodes and tonsils. Results showed that in both vaccinated groups the scores were on average 0.3, while in the unvaccinated-challenged control group IHC scores were on average 1.6.

qPCR results showed that in both vaccinated groups pigs had very little PCV2 present in serum, nasal- or fecal swabs, or tissue samples (lymph nodes, tonsils, and lungs). However, the control group became strongly positive for PCV2 nucleic acids after challenge.

Lawsonia Serology

Lawsonia serology for group 1 showed an increase in titer from SD22, while in the control group the Lawsonia titer showed a steady decrease.

PRRSV Serology

Serological results for PRRSV are typically expressed as an SP (Sample to Positive) ratio. When this ratio is above 0.4, a sample is considered positive for PRRSV seroconversion. The section of Table 4 for PRRSV represents these SP values. They show that animals in the positive control group 2 (PRRSV vaccine by id route) were strongly positive for PRRSV-seroconversion; nevertheless, animals in group 1 (4-way combination vaccine by im route) also reached good seroconversion rates. Unvaccinated controls hardly showed any seroconversion for PRRSV, as no SP ratios above 0.05 were found.

TABLE 4

Combined serological results of Example 4.2

| | Serology per group | SD0 | SD22 | SD28 | SD35 | SD43 |
|---|---|---|---|---|---|---|
| | PCV | | | | | |
| 1. | 4-way vaccine, im | 3.7 | 7.2 | 7.7 | 10.0 | 10.4 |
| 2. | Porcilis PCV ID + Porcilis PRRS ID | 3.7 | 7.0 | 8.1 | 9.5 | 9.9 |
| 3. | unvaccinated controls | 4.2 | 2.3 | 2.1 | 3.5 | 5.7 |
| | Lawsonia | | | | | |
| 1. | 4-way vaccine, im | 4.7 | 4.3 | 5.0 | 5.7 | 6.3 |
| 3. | unvaccinated controls | 3.3 | 3.3 | 3.3 | 2.9 | 2.9 |
| | PRRSV (SP ratios) | | | | | |
| 1. | 4-way vaccine, im | 0.0 | 0.9 | 1.3 | 1.3 | 1.4 |
| 2. | Porcilis PCV ID + Porcilis PRRS ID | 0.0 | 1.6 | 1.8 | 2.1 | 2.3 |
| 3. | unvaccinated controls | 0.0 | 0.0 | 0.0 | 0.0 | 0.0 |

Conclusions

Vaccination of pigs with the 4-way combination vaccine according to the invention, was effective in protecting against infection and signs of disease induced by a PCV2 challenge infection. Also, there was a good development of protection against Lawsonia and PRRSV, as measured by serology.

4.3. *Lawsonia* Efficacy

The 4-way combination vaccine was prepared as described above, using Prime Pac PRRS freeze dried vaccine.

Experimental Outline

Three groups of three week old pigs were vaccinated with the 4-way combination vaccine, and were given a challenge infection with virulent *Lawsonia* bacteria 5 weeks later. One group received the full 4-way vaccine, one other group received a control vaccine comprising all the same ingredients, except the *Lawsonia* antigen. The third group received the control vaccine, but no challenge as these were necropsied at the time of the challenge to confirm the absence of *Lawsonia* infection in the herd prior to challenge.

The groups were compared to determine the efficacy of a single dose of the combination-vaccine against disease caused by the *Lawsonia* challenge: ileitis, colonization of the ileum by *Lawsonia*, shedding, and effect on weight gain.

All pigs were evaluated every other day for local and systemic reactions for 21 days following the vaccination, or until resolution. Fecal samples were collected to confirm the absence of field infection by *Lawsonia* prior to the challenge. Blood samples were collected throughout the study to evaluate the antibody responses to vaccination and challenge, also fecal samples were collected for *Lawsonia* qPCR, and body weight data were recorded.

At three weeks post challenge (11 weeks of age) all remaining animals were necropsied and scores were determined of gross lesions of the ileum, and mucosal scrapings were collected for *Lawsonia* quantitative PCR (qPCR). Also a section of the ileum was collected for immunohistochemistry (IHC) and histopathology.

Details of the Experiment

Pigs were of mixed sex, and were a mixed American Yorkshire-Landrace-Duroc breed. Water and age-appropriate feed were provided at libitum.

The full 4-way vaccine comprised per 2 ml animal dose: 2.0 RP of Mhyo antigen; 6000 Elisa units of *Lawsonia* antigen/ml; 5.7 µg/ml of PCV2 Orf2 antigen; and $10^5$ TCID50 of PRRSV.

Just prior to challenge 2 pigs vaccinated with control vaccine were necropsied, to verify absence of any *Lawsonia* infection prior to challenge.

*Lawsonia* challenge was given by oral route, at 5 weeks post vaccination (about 8 weeks of age), with an inoculum of 4.6 10 Log TCID50 of live virulent *Lawsonia* per animal.

Lesion scoring of the ileum was done on a 2.5 cm section of the ileum, excised and collected in 10% buffered formalin, which was used for histopathological examination, and for the presence of *Lawsonia* by immunohistochemistry.

The rest of the ileum was opened and the mucosal surface was visually examined for the presence of *Lawsonia*-associated lesions of ileitis (also called Porcine Proliferative Enteritis or PPE) including mucosal proliferation with thickening of the intestinal wall, edema, hyperemia, congestion, necrosis and hemorrhaging. Gross lesions were given a score ranging from 0 (normal mucosa) to 5 (severe PPE with hemorrhaging and/or necrosis). Also ileum scrapings were collected and frozen until analysis.

Data Analysis:

The score for Ileitis was based on microscopic lesion score of ileitis by histopathology, and the gross lesion severity score of the ileum.

*Lawsonia* infection (colonization) was determined based on microscopic IHC score. qPCR was used to score for the presence of *Lawsonia* in rectal swabs and intestinal-mucosa scrapings, and for shedding in feces.

Results

Fecal Shedding:

No significant differences were found between the groups at 14 days post challenge (dpc). However fecal shedding results at 20 dpc showed that the vaccinated pigs were shedding significantly less *Lawsonia* than the placebo group at this time (p=0.0134), indicating earlier recovery by the vaccinates.

Colonisation:

qPCR of ileal scrapings collected at 20 dpc showed significantly more colonization by *Lawsonia* in the group receiving the placebo vaccine (p=0.0094).

Daily Weight Gain:

Following challenge, daily weight gain was also significantly improved in the 4-way vaccinated pigs, as compared to group receiving the placebo vaccine (p=0.0337).

Conclusion

Vaccination of pigs with the 4-way combination vaccine according to the invention, was effective in protecting against infection and signs of disease induced by a *Lawsonia* challenge infection.

4.4. PRRSV Efficacy

The 4-way combination vaccine was prepared as described above, and comprised PRRSV from reconstitution of an ampule of PrimePac™ PRRS vaccine, shortly before vaccination.

Experimental Outline

The objective of this study was to evaluate the immunogenicity of the PRRS fraction of the combination vaccine according to the invention, by vaccination of three week old pigs, and challenge with virulent PRRSV 4.5 weeks later.

Two groups of 25 healthy pigs each, negative for anti-PRRSV antibodies and PCV2 viremia, were vaccinated at three weeks of age by the intramuscular route with a 2 ml dose of the 4-way combination vaccine, or with a placebo (3-way) vaccine not comprising PRRSV. All antigens were present at estimated field dose levels.

At approximately 7.5 weeks of age, the pigs were challenged intranasally with PRRS virus strain NADC-20. Throughout the post-challenge period, pigs were evaluated for clinical observations and clinical scores, and blood and nasal swab samples were collected. At 14 days post-challenge, all pigs were euthanized and necropsied. Gross lesions of the lung were scored and lung sections and lymph nodes collected for histopathology and immunohistochemistry (IHC). The results were evaluated to determine the efficacy of a single dose of combination vaccine for the reduction of respiratory disease, viremia and/or shedding of PRRSV following a challenge infection.

Body weights were recorded at the time of vaccination, at challenge, and at end of test.

Details of the Experiment

PRRSV challenge was administered intranasally with 2 mL per nare of diluted challenge material. The challenge virus was prepared shortly before administration and kept on ice before and during use. The total challenge dose was approximately 4.2 $\log_{10}TCID_{50}$ per animal.

The full 4-way vaccine comprised per 2 ml animal dose: 2.0 RP of Mhyo antigen; 7000 Elisa units of *Lawsonia* antigen/ml; 5.7 µg/ml of PCV2 Orf2 antigen; and 10^5 TCID50 of PRRSV.

Data Analysis

Clinical observations of respiratory distress and lethargy were recorded immediately before and subsequently after the challenge. Clinical scores were indicated ranging from 0: normal, to 3: severe dyspnea and/or tachypnea and/or prominent abdominal breathing when stressed, whereby stress was induced by briefly inducing rapid movement of the pig.

Lung scoring was applied according to Halbur et. al. (1995, Vet. Pathol., vol. 32, p. 648-660 [Appendix 7, Ref. 1]). Macroscopic lung lesions were given a score to estimate the percentage of the lung affected by pneumonia. Each lung lobe was assigned a number of points to reflect the approximate volume percentage of the entire lung represented by that lobe. Ten possible points (5 for dorsal, 5 for ventral) were assigned each to the right anterior lobe, right middle lobe, anterior part of the left anterior lobe, and caudal part of the left anterior lobe. The accessory lobe was assigned 5 possible points, and 27.5 possible points (15 for dorsal and 12.5 for ventral) were assigned to each of the right and left caudal lobes to reach a total of 100 possible points. Gross lung lesion scores were recorded as the number of points that reflect the approximate volume percentage of that lobe affected by PRRS associated pneumonia. The total lung lesion score for each lung was calculated as the sum of the gross lung lesion scores of all lobes.

Lung samples were taken from each pig for histopathological examination, specifically: the tip of the left middle lobe, a piece of the accessory lobe, and the anterior part of the right caudal lobe. In addition, sections were taken from mediastinal and bronchial lymph nodes. The tissues were fixed in 10% neutral buffered formalin for histopathology and IHC.

Further collections were serum samples, for detection of anti-PRRSV antibodies; nasal swabs, for detection of PRRSV nucleic acid by a quantitative RT-PCR; and tissue samples, for microscopic analysis and IHC.

PRRSV samples were titrated on the MARC145 cell line. For each replicate, serial 10-fold dilutions were added to ten wells in a 96-well plate containing pre-formed cell monolayers, and the plates were incubated with 5% CO2 at 35-39° C. for five days. Next the plates were fixed and stained with an anti-PRRSV fluorescent antibody, and scored by IFT.

Outcome variables for vaccination efficacy were evaluated by analysis of post-challenge period clinical observations and clinical scores, body temperature, body weights, nasal shedding and viremia as determined by PCR, as well as macroscopic and microscopic analysis of lung lesions at 14 days post-challenge. Respiratory disease was assessed by macroscopic lung lesion scores Secondary variables of efficacy by tissue analysis by histopathology and IHC, maximum amount of viremia, maximum amount of shedding, weight gain following challenge, clinical observations following challenge, and respiratory clinical scores following challenge.

Results

The median of the lung lesion scores, in % of the lung involved, were: 20% for the placebo vaccine group, versus 7% for the 4-way vaccine group (p=0.0014).

The histopathology of the three collected lung samples was scored on a scale of 0 (normal) to 4 (severe interstitial pneumonia). The maximal scores were: 3 for the placebo vaccine group, versus 2 for the 4-way vaccine group (p=0.0010).

The lung sample immunohistochemistry was scored on a scale of 0 (no PRRSV-antigen positive cells) to 4 (>100 positive cells per tissue section). The maximum value of the scores of the three collected lung samples were 2 for the placebo vaccine group, versus 1 for the 4-way vaccine group (p=0.0006).

Conclusion

Vaccination of pigs with the 4-way combination vaccine according to the invention, was effective in protecting against infection and signs of disease induced by a PRRSV challenge infection.

The invention claimed is:

1. A combination vaccine comprising non-replicating antigen from porcine circovirus type 2 (PCV2) and live porcine reproductive and respiratory syndrome virus (PRRSV), wherein the vaccine is an oil-in-water emulsion comprising squalane and vitamin E-acetate; wherein the oil-in-water emulsion is a submicron emulsion.

2. The combination vaccine of claim 1, comprising squalane in an amount of between about 1 and about 9% w/v.

3. The combination vaccine of claim 1, comprising vitamin E-acetate in an amount of between about 1 and about 10% w/v.

4. The combination vaccine of claim 1, also comprising non-replicating antigen from *Mycoplasma hyopneumoniae* (Mhyo).

5. The combination vaccine of claim 1, also comprising non-replicating antigen from *Lawsonia intracellularis* (*Lawsonia*).

6. A kit of parts comprising at least two containers: one container comprising non-replicating antigen from PCV2 in an oil-in-water emulsion comprising squalane and vitamin E-acetate; and one container comprising live PRRSV in freeze-dried form; wherein the oil-in-water emulsion is a submicron emulsion.

7. A method for the preparation of the combination vaccine of claim 1, comprising the steps of:
    preparing an aqueous phase comprising non-replicating antigen from PCV2 and live PRRSV, and
    admixing said aqueous phase with an oily emulsion comprising squalane and vitamin E-acetate.

8. A method for the preparation of the combination vaccine of claim 1, comprising the steps of:
    preparing live PRRSV in a freeze-dried form,
    preparing an aqueous phase comprising non-replicating antigen from PCV2,
    admixing said aqueous phase with an oily emulsion comprising squalane and vitamin E-acetate, and
    reconstituting said freeze-dried live PRRSV with said admixture of aqueous phase and oily emulsion.

9. A method for the preparation of combination vaccine of claim 1, comprising the steps of:
    preparing an admixture of an aqueous phase comprising non-replicating antigen from PCV2, and of an oily emulsion comprising squalane and vitamin E-acetate, and reconstituting live PRRSV in a freeze-dried form with said admixture.

10. A method for vaccinating a swine against PCV2 and PRRSV, comprising administering to said swine the combination vaccine of claim 1.

11. A combination vaccine comprising non-replicating antigen from porcine circovirus type 2 (PCV2) and live porcine reproductive and respiratory syndrome virus (PRRSV), wherein the vaccine is an oil-in-water emulsion comprising squalane and vitamin E-acetate; wherein the amount of vitamin E-acetate is about 1 to about 10% w/v.

12. The combination vaccine of claim 11, wherein the amount of squalane is about 1 to about 9% w/v.

13. The combination vaccine of claim 11, further comprising non-replicating antigen from *Mycoplasma hyopneumoniae* (Mhyo).

14. The combination vaccine of claim 11, further comprising non-replicating antigen from *Lawsonia intracellularis* (Lawsonia).

\* \* \* \* \*